& # # United States Patent
Zhang et al.

(10) Patent No.: US 12,304,848 B2
(45) Date of Patent: May 20, 2025

(54) *PSEUDOMONAS STUTZERI* STRAIN, COMPOSITE MICROBIAL INOCULUM PREPARED FROM *PSEUDOMONAS STUTZERI* STRAIN AND USE OF COMPOSITE MICROBIAL INOCULUM

(71) Applicant: NANJING UNIVERSITY, Jiangsu (CN)

(72) Inventors: Xuxiang Zhang, Jiangsu (CN); Kailong Huang, Jiangsu (CN); Lin Ye, Jiangsu (CN); Hongqiang Ren, Jiangsu (CN)

(73) Assignee: NANJING UNIVERSITY, Jiangsu (CN)

( * ) Notice: Subject to any disclaimer, the term of this patent is extended or adjusted under 35 U.S.C. 154(b) by 629 days.

(21) Appl. No.: 17/623,257

(22) PCT Filed: Oct. 30, 2019

(86) PCT No.: PCT/CN2019/114172
§ 371 (c)(1),
(2) Date: Dec. 28, 2021

(87) PCT Pub. No.: WO2021/077453
PCT Pub. Date: Apr. 29, 2021

(65) Prior Publication Data
US 2022/0356098 A1 Nov. 10, 2022

(30) Foreign Application Priority Data
Oct. 24, 2019 (CN) .......................... 201911015530.2

(51) Int. Cl.
*C02F 3/02* (2023.01)
*C02F 3/34* (2023.01)
*C12N 1/20* (2006.01)
*C02F 103/06* (2006.01)
*C12R 1/38* (2006.01)

(52) U.S. Cl.
CPC ................ *C02F 3/341* (2013.01); *C02F 3/02* (2013.01); *C12N 1/205* (2021.05); *C02F 2103/06* (2013.01); *C12R 2001/38* (2021.05)

(58) Field of Classification Search
CPC . C02F 3/341; C02F 3/02; C12N 1/205; C12R 2001/38
See application file for complete search history.

(56) References Cited
U.S. PATENT DOCUMENTS
2016/0222280 A1* 8/2016 Kohr .................. C12N 1/26

FOREIGN PATENT DOCUMENTS
| CN | 101705202 | 5/2010 |
|---|---|---|
| CN | 101724594 | 6/2010 |
| CN | 103773723 | 5/2014 |
| CN | 110029071 | 7/2019 |

OTHER PUBLICATIONS
"International Search Report (Form PCT/ISA/210) of PCT/CN2019/114172" mailed on Jul. 29, 2020, with English translation thereof, pp. 1-8.

* cited by examiner

*Primary Examiner* — Lynn Y Fan
(74) *Attorney, Agent, or Firm* — JCIP GLOBAL INC.

(57) ABSTRACT

The present invention discloses a *Pseudomonas stutzeri* strain, named *Pseudomonas stutzeri* EBT-2, which was deposited in China Center for Type Culture Collection under Deposit No. CCTCC M 2019731 on Sep. 17, 2019. The present invention also discloses a composite microbial inoculum which is prepared by mixing an expanded culture solution of a *Pseudomonas balearica* EBT-1 with Deposit No. CCTCC M 2019730 and an expanded culture solution of the *Pseudomonas stutzeri* EBT-2 with Deposit No. CCTCC M 2019731 in a volume ratio of 1:1. The present invention finally discloses use of the composite microbial inoculum in treating membrane concentrate of landfill leachate. The composite microbial inoculum is capable of implementing high-efficiency biological denitrification of the membrane concentrate of landfill leachate.

5 Claims, 1 Drawing Sheet
Specification includes a Sequence Listing.

PSEUDOMONAS STUTZERI STRAIN, COMPOSITE MICROBIAL INOCULUM PREPARED FROM PSEUDOMONAS STUTZERI STRAIN AND USE OF COMPOSITE MICROBIAL INOCULUM

CROSS-REFERENCE TO RELATED APPLICATION

This application is a 371 of international application of PCT application serial no. PCT/CN2019/114172, filed on Oct. 30, 2019, which claims the priority benefit of China application no. 201911015530.2, filed on Oct. 24, 2019. The entirety of each of the above-mentioned patent applications is hereby incorporated by reference herein and made a part of this specification.

TECHNICAL FIELD

The present invention relates to the field of wastewater treatment, and particularly, to a *Pseudomonas stutzeri* strain, a composite microbial inoculum prepared from the *Pseudomonas stutzeri* strain and use of the composite microbial inoculum in treating membrane concentrate of landfill leachate.

BACKGROUND

Landfill leachate is a kind of high-concentration organic wastewater with complicated composition, which has the characteristics of poor biodegradability, high ammonia nitrogen concentration, and rich content of toxic and harmful substances. The control standards of environmental water quality become stricter. Especially, in October, 2009, the issue of Technical Specifications of Municipal Landfill Leachate Treatment Engineering (Draft for Comments) proposed that the membrane treatment should be the major of deep treatment process, and further confirmed the standardization trend of the membrane process. As the prominent process, the membrane deep treatment process will generate about 15%-30% of membrane concentrate. The membrane concentrate of landfill leachate mainly comprises humic substances, which appears brownish-black (yellow). The COD is usually between 1000-5000 mg/L, the total nitrogen concentration is between 500-2500 mg/L. It contains a large amount of inorganic ions. The TDS is between 20,000-60,000 mg/L and the electrical conductivity is 40,000-50,000 µS/cm. The salinity in the membrane concentrate of landfill leachate may reach more than 3%, seriously affecting the internal osmotic pressure of microorganisms. The high salinity hinders substance absorption, greatly reduces the growth rate and viability of microorganisms, and influences biochemical treatment efficiency of wastewater. The total nitrogen in the membrane concentrate of landfill leachate is mainly derived from the concentrate of landfill leachate after passing through a multi-stage membrane. Most of ammonia nitrogen in the wastewater is converted into nitrate nitrogen through nitrification, the nitrate nitrogen can make up more than 90% of the total nitrogen of the concentrate.

Biological denitrification is the most effective method for denitrification at present. The aerobic denitrifying bacterium *Pseudomonas balearica* EBT-1 can implement high-efficiency biological denitrification in membrane concentrate of landfill leachate. However, with the accumulation of nitrite nitrogen during the denitrification process, the denitrification rate is greatly decreased. How to accelerate the denitrification of nitrite nitrogen, consume nitrite nitrogen quickly and reduce the accumulation of nitrite nitrogen in the system is the key to further improving the efficiency of denitrification.

SUMMARY OF INVENTION

Purpose: The present invention is intended to solve the technical problem of providing a *Pseudomonas stutzeri* strain.

The present invention is further intended to solve the technical problem of providing a composite microbial inoculum prepared from the *Pseudomonas stutzeri* strain.

The present invention is eventually intended to solve the technical problem of providing use of the composite microbial inoculum in treating membrane concentrate of landfill leachate.

To solve the aforementioned technical problems, the present invention provides:

A *Pseudomonas stutzeri* strain named as *Pseudomonas stutzeri* EBT-2, with the classification name of *Pseudomonas stutzeri* and the strain number of EBT-2. It is deposited in China Center for Type Culture Collection (Deposit No. CCTCC M 2019731) at Wuhan University (Address of China Center for Type Culture Collection: No. 299 Bayi Road, Wuchang District, Wuhan City, Hubei Province) on Sep. 17, 2019.

The strain has the following biological properties: The *Pseudomonas stutzeri* EBT-2 is derived from the activated sludge in a biochemical wastewater treatment system for landfill leachate with high salinity. It grows well in an LB culture medium under an aerobic condition at 35° C. after isolation. The colonies have a round but irregular shape, a diameter of 0.5-2 mm, a yellowish color, a translucent appearance and a slightly wet surface. The stain is gram-negative and shows a short rod shape under the microscope.

Through 16S rRNA sequencing, BLAST analysis and NCBI retrieval, it turns out that the similarity of the gene sequence of the *Pseudomonas* strain EBT-2 obtained in the present invention to *Pseudomonas stutzeri* is as high as 99%, and thus the strain is identified as *Pseudomonas stutzeri*.

The composite microbial inoculum is prepared by mixing an expanded culture of a *Pseudomonas balearica* EBT-1 with Deposit No. CCTCC M 2019730 and an expanded culture of the *Pseudomonas stutzeri* EBT-2 with Deposit No. CCTCC M 2019731 in a volume ratio of 1:1.

The preparation method for the composite microbial inoculum comprises:

(1) inoculating *Pseudomonas balearica* EBT-1 with Deposit No. CCTCC M 2019730 and *Pseudomonas stutzeri* EBT-2 with Deposit No. CCTCC M 2019731 separately into a culture medium, and incubating in an aerobic condition at 30-35° C. for 24-32 h to give an EBT-1 expansion product and an EBT-2 expansion product, respectively; and (2) mixing the obtained expansion products in a volume ratio of EBT-1:EBT-2=1:1 to give the composite microbial inoculum.

In the step (1), the inoculation amount of *Pseudomonas balearica* EBT-1 with Deposit No. CCTCC M 2019730 in the culture medium is 3%-5%.

In the step (1), the inoculation amount of *Pseudomonas stutzeri* EBT-2 with Deposit No. CCTCC M 2019731 in the culture medium is 3%-5%.

In the step (1), each liter of the culture medium comprises the following mass fractions: 10-12.5 parts of corn syrup, 5 parts of yeast extract, 1 part of dipotassium phosphate, 10-12.5 parts of sodium chloride, 0.5-2.5 parts of anhydrous sodium acetate and 0.03 part of magnesium sulfate. The culture medium is specially prepared for the salt-resistant *Pseudomonas* strain domesticated in the present invention. As such, when the *Pseudomonas* strain is incubated with the culture medium, the salt-resistant property of the *Pseudomonas* strains can be retained, the strain can grow quickly as well. The corn syrup in the culture medium contains abundant soluble proteins and amino acids. Through controlling the salinity of the culture medium, necessary elements for internal amino acid synthesis are enriched for retaining the salt resistance of the microorganisms while necessary nitrogen is enriched for quick growth of the microorganism.

The preparation method for the culture medium for aerobic denitrifying bacteria comprises: dissolving required parts of corn syrup, yeast extract, dipotassium phosphate, sodium chloride, anhydrous sodium acetate and magnesium sulfate in 1000 parts of water, adjusting the pH to 6.5-7.5 with alkali, and sterilizing at 121° C. for 20 min to obtain the culture medium.

Use of the composite microbial inoculum in treating membrane concentrate of landfill leachate.

A *Pseudomonas balearica* strain named as *Pseudomonas balearica* EBT-1, with the classification name of *Pseudomonas balearica* and the strain number of EBT-1, is deposited in China Center for Type Culture Collection (Deposit No. CCTCC M 2019730) at Wuhan University (Address of China Center for Type Culture Collection: No. 299 Bayi Road, Wuchang District, Wuhan City, Hubei Province) on Sep. 17, 2019.

The strain has the following biological properties: The *Pseudomonas balearica* EBT-1 strain is derived from activated sludge in a biochemical wastewater treatment system for high-salt landfill leachate, and it grows well in LB culture medium in aerobic condition at 35° C. after isolation. The colonies have a round but irregular shape, a diameter of 2-5 mm, a white color, an opaque appearance and a surface with inward folds. The stain is gram-negative, and demonstrates a rod shape under the microscope.

The strain EBT-1 described herein, through 16S rRNA sequencing, BLAST analysis and NCBI retrieval, demonstrates a gene sequence similarity as high as 99% to *Pseudomonas balearica*, and thus the strain is identified as *Pseudomonas balearica*.

Beneficial Effects: The composite microbial inoculum disclosed herein is capable of implementing high-efficiency biological denitrification of the membrane concentrate of landfill leachate; in addition, after 24-32 h of incubation with the culture medium for fast expansion, the effective concentration of the functional strain disclosed herein may reach above 108 CFU/mL, which indicates that the culture medium of the present invention can greatly increase the amount of functional strain and shorten the cultivation period of the functional strain as compared with a conventional denitrification medium.

DESCRIPTION OF EMBODIMENTS

Figure 1:
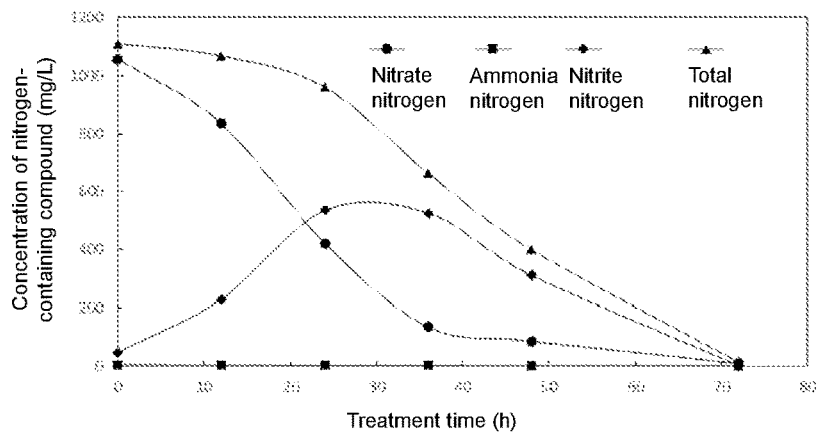
FIG. 1 illustrates the efficiency of the deep denitrification in the membrane concentrate of landfill leachate by EBT-1 in Example 3.

The technical solutions of the present invention are further described in detail below with reference to drawings and specific embodiments.

Example 1: Isolation and Identification of the Strain

The strain EBT-1 is an aerobic denitrifying bacterium with denitrifying activity screened out from activated sludge of the high-salt wastewater treatment system of a refuse incineration facility.

The method for separation and screening comprised the following steps: took 5 g of activated sludge from a biochemical wastewater treatment system for high-salt landfill leachate and inoculated it into a DM inorganic salt culture medium with a nitrate nitrogen concentration of 100 mg/L at a temperature of 35° C., and incubated on a shaker at 150 rpm for 1 day to give the first bacterial culture; inoculated the first bacterial culture into a DM inorganic salt culture medium with the nitrate nitrogen concentration of 200 mg/L at an inoculation amount of 5% (volume fraction), and incubated on a shaker at 150 rpm at 35° C. for 1 day to give the second bacterial culture; inoculated the second bacterial culture into a DM inorganic salt culture medium with the nitrate nitrogen concentration of 300 mg/L at the inoculation amount of 5%, and incubated on a shaker at 150 rpm at 35° C. for 1 day to give the third bacterial culture; spread a proper amount of the third bacterial liquid on a solid DM inorganic salt culture medium, and incubated at 35° C. to select colonies with higher growth rate, streaked with the selected colonies on a solid DM medium containing bromothymol blue, and incubated at 35° C. to obtain a blue-stained strain; the selected colonies were further isolated by streaking on a solid DM culture medium until a single bacterial colony was screened out.

The bacterial colony above-mentioned is the *Pseudomonas balearica* EBT-1 of the present invention, which is capable of high-efficiency biological denitrification of the membrane concentrate of landfill leachate.

The strain EBT-1 has the following characteristics: The strain grows well in LB culture medium in aerobic condition at 35° C. after isolation. The colonies have a round but irregular shape, a diameter of 2-5 mm, a white color, an opaque appearance and a surface with inward folds. The stain is gram-negative and demonstrates a rod shape under the microscope.

The complete sequence of the 16S rRNA of the EBT-1 strain obtained by PCR amplification is as follows (SEQ ID NO. 1):

```
gcttgcggcagactacacatgcagtcgagcggcag cgggtccttcgggatgccggcgagcggcggacggg tgagtaatgcctaggaatctgcctggtagtggggg ataactcggggaaactcgagctaataccgcatacg tcctacgggagaaagcgggggatcttcggacctcg cgctaccagatgagcctaggtcggattagctagtt ggtgaggtaaaggctcaccaaggcgacgatccgta gctggtctgagaggatgatcagccacactggaact
```

```
-continued
gagacacggtccagactcctacgggaggcagcagt gggg aatattggacaatgggcgaaagcctgatcca gccatgccgcgtgtgtgaagaaggtcttcggattg taaagcactttaagttgggaggaagggcagtaagc taatatcttgctgttttgacgttaccgacagaata agcaccggctaacttcgtgccagcagccgcggtaa tacgaagggtgcaagcgttaatcggaattactggg cgtaaagcgcgcgtaggtggtttgataagttggat gtgaaagccccgggctcaacctgggaattgcatcc aaaactgtctgactagagtatggcagagggtggtg gaatttcctgtgtagcggtgaaatgcgtagatata ggaaggaacaccagtggcgaaggcgaccatctggg ctaatactgacactgaggtgcgaaagcgtggggag caaacaggattagataccctggtagtccacgccgt aaacgatgtcgactagccgttgggatccttgagat cttagtggcgcagctaacgcattaagtcgaccgcc tggggagtacggccgcaaggttaaaactcaaatga attgacggggcccgcacaagcggtggagcatgtg gtttaattcgaagcaacgcgaagaaccttaccagg ccttgacatgcagagaactttccagagatggattg gtgccttcgggaactctgacacaggtgctgcatgg ctgtcgtcagctcgtgtcgtgagatgttgggttaa gtcccgtaacgagcgcaacccttgtccttagttac cagcacgttaaggtgggcactctaaggagactgcc ggtgacaaaccggaggaaggtggggatgacgtcaa gtcatcatggcccttacggcctgggctacacacgt gctacaatggtcggtacaaagggttgccaagccgc gaggtggagctaatcccataaaaccgatcgtagtc cggatcgcagtctgcaactcgactgcgtgaagtcg gaatcgctagtaatcgtgaatcagaatgtcacggt gaatacgttcccgggccttgtacacaccgcccgtc acaccatgggtagtgggttgctccagaagtaagcg aagtctaaccttcgggggacggtaccacggagat actg
```

Through alignment, the strain demonstrated a gene sequence similarity as high as 99% to *Pseudomonas balearica*, and was thus identified as *Pseudomonas balearica*.

Example 2: Expansion Culture of *Pseudomonas balearica* EBT-1

The culture medium used in expansion culture comprised the following components per liter of water: 10 g of corn syrup, 5 g of yeast extract, 10 g of sodium chloride, 2.5 g of anhydrous sodium acetate, 1 g of dipotassium phosphate and 0.03 g of magnesium sulfate, and the initial pH of the medium was 6.5.

The preparation process of the culture medium comprised the following steps: dissolved 10 g of corn syrup, 5 g of yeast extract, 10 g of sodium chloride, 2.5 g of anhydrous sodium acetate, 1 g of dipotassium phosphate and 0.03 g of magnesium sulfate in 1000 g of water, adjusted the pH to 6.5 with alkali, and sterilized the mixture at 121° C. for 20 min to give the culture medium.

Inoculated *Pseudomonas balearica* EBT-1 inoculum at an inoculation amount of 3%-5% (volume fraction) into a culture medium, and incubated at 30-35° C. for 28-32 h.

After the culture medium of the present invention was used for expansion, the bacteria liquid obtained by the expansion culture was counted by the dilution plate method, and the effective target bacterial amount was $5 \times 10^8$ to $1 \times 10^9$ CFU/mL.

Example 3: Analysis of Biological Denitrification by *Pseudomonas balearica* EBT-1 in Membrane Concentrate of Landfill Leachate The selected denitrifying bacteria (*Pseudomonas balearica* EBT-1) was expanded to give an inoculum. All the obtained inoculum was transferred into a new centrifuge tube, and centrifuged at 6000 rpm for 5 min. The supernatant was removed to get an activated solid inoculum. Added 200 mL of the membrane concentrate of landfill leachate with a salinity of 3.5% to a clean hypoxia bottle and then added anhydrous sodium acetate as the carbon source to make the carbon-nitrogen ratio of the waste liquid with 4:1. Finally *Pseudomonas balearica* EBT-1 was added with an inoculation amount of 0.4%, and was shaken at 150 rpm at 30° C.

The changes of total nitrogen in the membrane concentrate of landfill leachate during the reaction process were monitored, and the result was shown in FIG. 1. As shown in FIG. 1, after 72 hours of the treatment, the total nitrogen in the membrane concentrate of landfill leachate dropped from an initial concentration of 1110.74 mg/L to 13.37 mg/L, which indicated that the total nitrogen removal rate of *Pseudomonas balearica* EBT-1 in the membrane concentrate of landfill leachate of the present invention was as high as 99%.

Example 4: Isolation and Identification of the Strain

Activated sludge in the high-salt wastewater treatment system of a refuse incineration facility was taken as a research object, and from which aerobic denitrifying bacteria with denitrifying activity for degrading nitrite were screened out.

The method for separation and screening comprised the following steps: 5 g of activated sludge from a biochemical wastewater treatment system for the high-salt landfill leachate was inoculated into a DM inorganic salt culture medium with a nitrite nitrogen concentration of 100 mg/L, and was incubated for 2-3 days at 35° C. on a shaker of 150 rpm to give the first bacterial culture; the first bacterial culture was inoculated into a DM inorganic salt culture medium with the nitrite nitrogen concentration of 200 mg/L at an inoculation amount of 5% (volume fraction), and was incubated for 2-3 days at 35° C. on a shaker of 150 rpm to give the second bacterial culture; the second bacterial culture was inoculated into a DM inorganic salt culture medium with the nitrite nitrogen concentration of 300 mg/L at an inoculation amount of 5%, and was incubated for 2-3 days at 35° C. on a shaker of 150 rpm to give the third bacterial culture; a proper amount of the third bacterial liquid was spread on a solid DM inorganic salt culture medium with a nitrite nitrogen concentration of 300 mg/L, and incubated at 35° C.; colonies with higher growth rate was screened out, streaked on a solid DM medium containing bromothymol blue, and incubated at 35° C. to give colonies with blue plate; the selected colonies were further isolated by streaking on a solid DM culture medium until a single bacterial colony was selected. The bacterial colony is the *Pseudomonas stutzeri* EBT-2.

The *Pseudomonas stutzeri* EBT-2 of the present invention was derived from activated sludge in an anoxic tank of the wastewater treatment system for landfill leachate. Through inoculating, enriching, screening and isolating in a nitrite nitrogen-modified DM culture medium, an aerobic denitrifying bacterium with the capability of degrading nitrite and high denitrification activity was obtained, which is deposited in China Center for Type Culture Collection under Deposit CCTCC No. 2019731 on Sep. 17, 2019.

The strain has the following biological properties: The *Pseudomonas stutzeri* EBT-2 is derived from activated sludge in the wastewater treatment system for high-salt landfill leachate with the salinity above 3%, and grows well in an LB culture medium in an aerobic condition at 35° C. after isolation. The colonies have a round but irregular shape, a diameter of 0.5-2 mm, a yellowish color, a translucent appearance and a slightly wet surface. The stain is gram-negative and demonstrates a short rod shape under the microscope.

The complete sequence of the 16S rRNA of the EBT-2 strain obtained by PCR amplification is as follows (SEQ ID NO. 2):

tctggggcagactaacacatgcaagtcgagcggat gagtggagcttgctccatgattcagcggcggacgg gtgagtaatgcctaggaatctgcctggtagtgggg gacaacgtttcgaaaggaacgctaataccgcatac gtcctacgggagaaagtggggatcttcggacctc acgctatcagatgagcctaggtcggattagctagt tggtgaggtaaaggctcaccaaggcgacgatccgt aactggtctgagaggatgatcagtcacactggaac tgagacacggtccagactcctacgggaggcagcag tggggaatattggacaatgggcgaaagcctgatcc agccatgccgcgtgtgtgaagaaggtcttcggatt gtaaagcacttttaagttgggaggaagggcagtaag ttaataccttgctgttttgacgttaccaacagaat aagcaccggctaacttcgtgccagcagccgcggta atacgaagggtgcaagcgttaatcggaattactgg gcgtaaagcgcgcgtaggtggttcgttaagttgga tgtgaaagccccgggctcaacctgggaactgcatc caaaactggcgagctagagtatggcagagggtggt ggaatttcctgtgtagcggtgaaatgcgtagatat aggaaggaacaccagtggcgaaggcgaccacctgg gctaatactgacactgaggtgcgaaagcgtgggga gcaaacaggattagataccctggtagtccacgccg taaacgatgtcgactagccgttgggatccttgaga tcttagtggcgcagctaacgcattaagtcgaccgc ctggggagtacggccgcaaggttaaaactcaaatg aattgacggggcccgcacaagcggtggagcatgt ggtttaattcgaagcaacgcgaagaaccttaccag gccttgacatgcagagaactttccagagatggatt ggtgccttcgggaactctgacacaggtgctgcatg gctgtcgtcagctcgtgtcgtgagatgttgggtta agtcccgtaacgagcgcaaccctt gtccttagtta ccagcacgttaaggtgggcactctaaggagactgc cggtgacaaaccggaggaaggtggggatgacgtca agtcatcatggcccttacggcctgggctacacacg tgctacaatggtcggtacaaagggttgccaagccg cgaggtggagctaatcccataaaaccgatcgtagt ccggatcgcagtctgcaactcgactgcgtgaagtc ggaatcgctagtaatcgtgaatcagaatgtcacgg tgaatacgttcccgggccttgtacacaccgcccgt cacaccatgggagtgggttgctccagaagtagcta gtctaaccttcgggggggacggtaccacggagatag g Through alignment, the strain demonstrates a gene sequence similarity over 99% to *Pseudomonas stutzeri*, and is thus identified as *Pseudomonas stutzeri*.

Example 5: Expansion Culture of *Pseudomonas stutzeri* EBT-2

The culture medium used in expansion culture comprised the following components per liter of water: 12 g of corn syrup, 5 g of yeast extract, 12.5 g of sodium chloride, 0.5 g of anhydrous sodium acetate, 1 g of dipotassium phosphate and 0.03 g of magnesium sulfate, initial pH 7.0.

The preparation process of the culture medium comprised the following steps: 12 g of corn syrup, 5 g of yeast extract, 12.5 g of sodium chloride, 0.5 g of anhydrous sodium acetate, 1 g of dipotassium phosphate and 0.03 g of magnesium sulfate were dissolved in 1000 g of water, the pH was adjusted to 7.0 with an alkali, and the mixture was sterilized at 121° C. for 20 min to give the expansion culture medium.

*Pseudomonas stutzeri* EBT-2 inoculum was inoculated at an inoculation amount of 3%-5% into the aforementioned culture medium, and incubated at 30-35° C. for 28-32 h.

The bacteria in cultures were calculated by plate dilution counting, and the effective target bacterial amount was $1 \times 10^8$ CFU/mL or higher.

Example 6: Analysis of Denitrification by Pseudomonas stutzeri EBT-2 with Nitrite Nitrogen as Nitrogen Source The selected denitrifying *Pseudomonas stutzeri* EBT-2 was expanded to give an inoculum. All the obtained inoculum was transferred into a new centrifuge tube, and centrifuged at 6000 rpm for 5 min. The supernatant was removed to obtain an activated solid inoculum. Took a clean hypoxia bottle and added 200 mL of a DM culture medium in it with nitrite as nitrogen source, anhydrous sodium acetate as carbon source and the carbon to nitrogen ratio was 4:1. Finally *Pseudomonas stutzeri* EBT-2 was added with an inoculation amount of 0.4%, and the hypoxia bottle was shaken at 150 rpm at 30° C.

Figure 2:
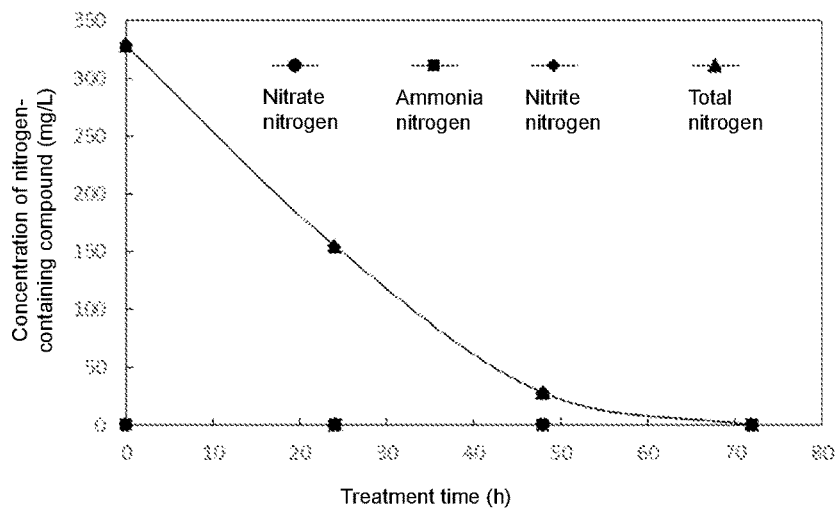
FIG. 2 illustrates the efficiency of the denitrification with nitrite nitrogen as the nitrogen source by EBT-2 in Example 6.

The changes in total nitrogen in the culture medium during the reaction process were monitored, and the result was shown in FIG. 2. As shown in FIG. 2, after 72-hour treatment, *Pseudomonas stutzeri* EBT-2 was capable to reduce the total nitrogen content in the medium from 329 mg/L to 0.06 mg/L, suggesting that *Pseudomonas stutzeri* EBT-2 has a higher reduction rate of nitrite nitrogen.

Example 7

The expansion products obtained in Example 2 and 5 were well mixed in a volume ratio of EBT-1:EBT-2=1:1 to obtain a composite microbial inoculum.

The denitrifying performance of the composite microbial inoculum for treating membrane concentrate of landfill leachate was monitored, which comprised the following steps:

Step 1: a certain amount of the composite microbial inoculum was centrifuged at 6000 rpm for 5 min, and the precipitate was resuspended with the membrane concentrate of landfill leachate at an inoculation amount of 0.4% to give an inoculum;

Step 2: two clean flasks numbered 1# (treatment group: added with the composite microbial inoculum) and 2# (control group: not added with the composite microbial inoculum) were added with the membrane concentrate of landfill leachate containing 1188 mg/L of total nitrogen and anhydrous sodium acetate (COD/TN=4:1) to a total volume of 200 mL for each;

Step 3: the measuring system in Step 2 was incubated on a shaker at 150 rpm under 28° C., the total nitrogen in the system was detected after 0 h, 5 h, 20 h, 24 h and 48 h, and the total nitrogen removal of the treated membrane concentrate of landfill leachate was calculated. The result was shown in FIG. 3.

Figure 3:
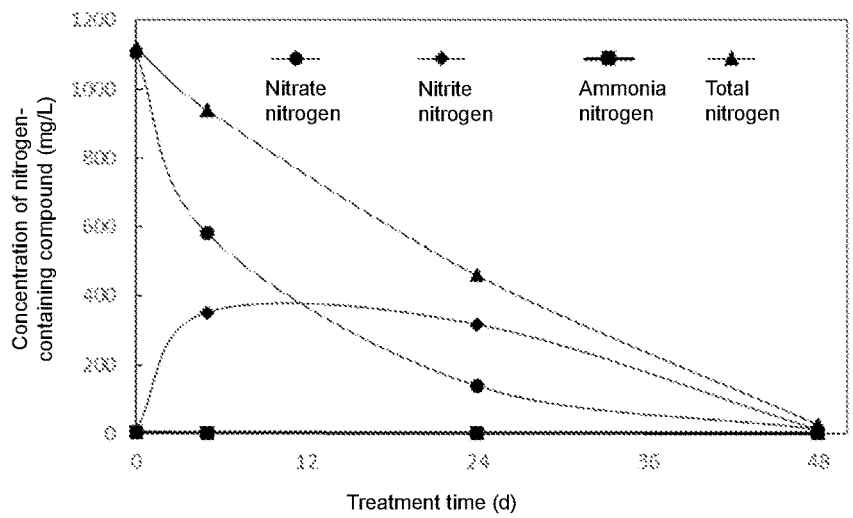
FIG. 3 illustrates the efficiency of the deep denitrification in the membrane concentrate of landfill leachate by the composite microbial inoculum in Example 7.

As shown in FIG. 3, 48 h after the treatment with the composite microbial inoculum prepared by mixing expansion products in proportion, the total nitrogen in the effluent of the membrane concentrate of landfill leachate was 24.95 mg/L, and the total nitrogen removal of the compound microbial inoculum in the membrane concentrate of landfill leachate was as high as 97% or more. Compared to separate treatments with the two bacteria, the denitrification efficiency of the composite microbial inoculum was obviously improved in the same condition. Since the energy required by the nitrate reductase (Nar) for reducing nitrate to nitrogen was lower than the energy required by the nitrite nitrogen reductase (Nir) for reducing nitrite to nitrogen, microorganisms would preferentially reduce nitrate, thereby causing a delayed reduction and accumulation of nitrite. *Pseudomonas stutzeri* EBT-2 can use nitrite and nitrate as denitrification nitrogen source. After nitrite rapidly accumulated to a certain extent, nitrite was reduced preferentially, which greatly improved the denitrification rate.

The composite microbial inoculum disclosed herein has high total nitrogen removal efficiency (particularly nitrate nitrogen) in wastewater, and can effectively solve the problem of deep denitrification in the membrane concentrate of landfill leachate.

What is claimed is:

1. A preparation method for a composite microbial inoculum, comprising:
    (1) inoculating *Pseudomonas balearica* EBT-1 with Deposit No. CCTCC M 2019730 and *Pseudomonas stutzeri* EBT-2 with Deposit No. CCTCC M 2019731 separately into a culture medium, and incubating in an aerobic condition at 30-35° C. for 24-32 h to give an EBT-1 expansion product and an EBT-2 expansion product, respectively; and
    (2) mixing the EBT-1 expansion product and the EBT-2 expansion product in a volume ratio of 1:1 to give the composite microbial inoculum.

2. The preparation method for the composite microbial inoculum according to claim 1, wherein following the step (1), the inoculation amount of *Pseudomonas balearica* EBT-1 with Deposit No. CCTCC M 2019730 in the culture medium is 3%-5%.

3. The preparation method for the composite microbial inoculum according to claim 1, wherein following the step (1), the inoculation amount of *Pseudomonas stutzeri* EBT-2 with Deposit No. CCTCC M 2019731 in the culture medium is 3%-5%.

4. The preparation method for the composite microbial inoculum according to claim 1, wherein following the step (1), the culture medium comprises: 1000 parts of water, 10 parts of corn syrup, 5 parts of yeast extract, 1 part of dipotassium phosphate, 12.5 parts of sodium chloride, 2.5 parts of anhydrous sodium acetate and 0.03 part of magnesium sulfate.

5. The preparation method for the composite microbial inoculum according to claim 1, wherein the initial pH of the culture medium is 6.5-7.5.

* * * * *

SEQUENCE LISTING

```
<160> NUMBER OF SEQ ID NOS: 2

<210> SEQ ID NO 1
<211> LENGTH: 1436
<212> TYPE: DNA
<213> ORGANISM: Pseudomonas stutzeri

<400> SEQUENCE: 1
tctggggcag actaacacat gcaagtcgag cggatgagtg gagcttgctc catgattcag      60
cggcggacgg gtgagtaatg cctaggaatc tgcctggtag tggggggacaa cgtttcgaaa    120 ggaacgctaa taccgcatac gtcctacggg agaaagtggg ggatcttcgg acctcacgct    180
atcagatgag cctaggtcgg attagctagt tggtgaggta aaggctcacc aaggcgacga    240
tccgtaactg gtctgagagg atgatcagtc acactggaac tgagacacgg tccagactcc    300
tacgggaggc agcagtgggg aatattggac aatgggcgaa agcctgatcc agccatgccg    360
cgtgtgtgaa gaaggtcttc ggattgtaaa gcactttaag ttgggaggaa gggcagtaag    420
ttaataccct gctgttttga cgttaccaac agaataagca ccggctaact tcgtgccagc    480
agccgcggta atacgaaggg tgcaagcgtt aatcggaatt actgggcgta aagcgcgcgt    540
aggtggttcg ttaagttgga tgtgaaagcc ccgggctcaa cctgggaact gcatccaaaa    600
ctggcgagct agagtatggc agagggtggt ggaatttcct gtgtagcggt gaaatgcgta    660
```

-continued

```
gatataggaa ggaacaccag tggcgaaggc gaccacctgg gctaatactg acactgaggt        720
gcgaaagcgt ggggagcaaa caggattaga taccctggta gtccacgccg taaacgatgt        780
cgactagccg ttgggatcct tgagatctta gtggcgcagc taacgcatta agtcgaccgc        840
ctggggagta cggccgcaag gttaaaactc aaatgaattg acggggcccc gcacaagcgg        900
tggagcatgt ggtttaattc gaagcaacgc gaagaacctt accaggcctt gacatgcaga        960
gaactttcca gagatggatt ggtgccttcg ggaactctga cacaggtgct gcatggctgt       1020
cgtcagctcg tgtcgtgaga tgttgggtta agtcccgtaa cgagcgcaac ccttgtcctt       1080
agttaccagc acgttaaggt gggcactcta aggagactgc cggtgacaaa ccggaggaag       1140
gtggggatga cgtcaagtca tcatggccct tacggcctgg gctacacacg tgctacaatg       1200
gtcggtacaa agggttgcca agccgcgagg tggagctaat cccataaaac cgatcgtagt       1260
ccggatcgca gtctgcaact cgactgcgtg aagtcggaat cgctagtaat cgtgaatcag       1320
aatgtcacgg tgaatacgtt cccgggcctt gtacacaccg cccgtcacac catgggagtg       1380
ggttgctcca gaagtagcta gtctaacctt cgggggacg gtaccacgga gatagg           1436
```

<210> SEQ ID NO 2
<211> LENGTH: 1439
<212> TYPE: DNA
<213> ORGANISM: Pseudomonas balearica

<400> SEQUENCE: 2

```
gcttgcggca gactacacat gcagtcgagc ggcagcgggt ccttcgggat gccggcgagc         60
ggcggacggg tgagtaatgc ctaggaatct gcctggtagt gggggataac tcgggggaaac       120
tcgagctaat accgcatacg tcctacggga aaagcgggg gatcttcgga cctcgcgcta        180
ccagatgagc ctaggtcgga ttagctagtt ggtgaggtaa aggctcacca aggcgacgat       240
ccgtagctgg tctgagagga tgatcagcca cactggaact gagacacggt ccagactcct       300
acggaggca gcagtgggga atattggaca atgggcgaaa gcctgatcca gccatgccgc       360
gtgtgtgaag aaggtcttcg gattgtaaag cactttaagt tgggaggaag ggcagtaagc       420
taatatcttg ctgttttgac gttaccgaca gaataagcac cggctaactt cgtgccagca       480
gccgcggtaa tacgaagggt gcaagcgtta atcggaatta ctgggcgtaa agcgcgcgta       540
ggtggtttga taagttggat gtgaaagccc cgggctcaac ctgggaattg catccaaaac       600
tgtctgacta gagtatggca gagggtggtg aatttcctg tgtagcggtg aaatgcgtag        660
atataggaag gaacaccagt ggcgaaggcg accatctggg ctaatactga cactgaggtg       720
cgaaagcgtg gggagcaaac aggattagat accctggtag tccacgccgt aaacgatgtc       780
gactagccgt tgggatcctt gagatcttag tggcgcagct aacgcattaa gtcgaccgcc       840
tggggagtac ggccgcaagg ttaaaactca aatgaattga cggggcccg cacaagcggt        900
ggagcatgtg gtttaattcg aagcaacgcg aagaacctta ccaggccttg acatgcagag      960
aactttccag agatggattg gtgccttcgg gaactctgac acaggtgctg catggctgtc      1020
gtcagctcgt gtcgtgagat gttgggttaa gtcccgtaac gagcgcaacc cttgtcctta      1080
gttaccagca cgttaaggtg ggcactctaa ggagactgcc ggtgacaaac cggaggaagg      1140
tggggatgac gtcaagtcat catggccctt acggcctggg ctacacacgt gctacaatgg      1200
tcggtacaaa gggttgccaa gccgcgaggt ggagctaatc ccataaaacc gatcgtagtc      1260
```

```
cggatcgcag tctgcaactc gactgcgtga agtcggaatc gctagtaatc gtgaatcaga    1320
atgtcacggt gaatacgttc ccgggccttg tacacaccgc ccgtcacacc atgggtagtg    1380
ggttgctcca gaagtaagcg aagtctaacc ttcggggga cggtaccacg gagatactg     1439
```